United States Patent [19]
Roemmele et al.

[11] Patent Number: 5,929,287
[45] Date of Patent: Jul. 27, 1999

[54] CHLORINATION OF SUBSTITUTED ALKENES USING TRICHLOROISOCYANURIC ACID

[75] Inventors: Renee Caroline Roemmele, Maple Glen; Heather Lynnette Rayle, North Wales, both of Pa.

[73] Assignee: Rohm and Haas Company, Philadelphia, Pa.

[21] Appl. No.: 09/059,062

[22] Filed: Apr. 13, 1998

Related U.S. Application Data

[60] Provisional application No. 60/043,352, Apr. 15, 1997.

[51] Int. Cl.$^6$ .................................................. C07C 45/00
[52] U.S. Cl. ..................... 568/407; 568/403; 570/189; 546/190; 548/579; 556/466; 585/23
[58] Field of Search ..................... 568/403, 407, 568/408, 419, 361, 364, 366, 376, 379, 380, 405, 406; 544/190; 548/579; 556/466; 585/23; 570/189

[56] References Cited

FOREIGN PATENT DOCUMENTS 2 633 614   6/1988   France .
58-052231   3/1983   Japan .

OTHER PUBLICATIONS

Mura et al, Tetrahedron Letters, 50, 4433–4436, 1975.
March et al, Advanced Organic Chemistry, third edition, pp. 66–68 and 527–529, 1985.

Chlorination of Ketones With Trichloroisocyanuric Acid, Gene A. Hiegel, et al., *Synthetic Communications*, 15(3), 385–392 (1985).

Hambly, G.F. et al., "Reactions of Enol Silyl Ethers with N–Halosuccinimide—A Stepwise Process," *Tetrahedron Lett.*, 1986, vol. 27, pp. 2563–2566, XP–002071278.

Seufert, W. et al., "Halogenation of Enamines—Synthesis of β–Halo Immonium Halides," *Chem. Ber.*, 1979, vol. 112, pp. 1670–1676, XP 000602265.

Motohashi, S et al., "Lead(IV) Acetate/Metal Halide Reagents; I. Synthesis of α–Haloketones," *Synthesis*, 1982, pp. 1021–1023, XP002071279.

*Primary Examiner*—Shailendra Kumar
*Assistant Examiner*—Sreeni Padmanabhan
*Attorney, Agent, or Firm*—Clark R. Carpenter

[57] ABSTRACT

This invention relates to a process for the selective monochlorination or dichlorination of certain substituted alkenes using trichloroisocyanuric acid. The chlorinated alkenes can be easily hydrolyzed to provide α-monochloroketones or α,α-dichloroketones with a high degree of selectivity. The resulting α-monochloroketones or α,α-dichloroketones have utility as fungicides or function as useful intermediates for fungicides.

7 Claims, No Drawings

CHLORINATION OF SUBSTITUTED ALKENES USING TRICHLOROISOCYANURIC ACID

This Application is a continuation of Provisional Application No. 60/043,352 Apr. 15, 1997.

This invention relates to an inexpensive and convenient process to prepare certain substituted 1-chloroalkenes from substituted alkenes using trichloroisocyanuric acid (TCIA) as a novel selective chlorinating agent. The substituted 1-chloroalkenes can be readily hydrolyzed to α-chloroketones which are useful as fungicides.

The selective preparation of monochlorinated ketones and aldehydes is difficult. Typically, the direct chlorination of carbonyl compounds in the presence of chlorine gas or other chlorine sources yields a mixture of unchlorinated, dichlorinated and monochlorinated carbonyl compounds. Chloroketones also have been prepared by trapping of enolates generated from carbonyl compounds. However, preparation of the enolates typically requires the use of strong bases which are expensive and difficult to handle, such as butyllithium, sodium amide and the like, at extremely low temperatures, typically about −78° C.

We have identified a chlorinating agent, TCIA, which affords good selectivity for monochlorination of alkenes, such as enol ethers, enol esters, enamines, 5-methylene-1,3-oxazin-2-ones, 5-methyleneoxazolines and the like, which are precursors to carbonyl compounds. The selectivity observed is better than that obtained with chlorine gas, which is typically employed in chlorination reactions. TCIA is an inexpensive commercially available compound which is much less hazardous to handle than chlorine gas.

FR 2,633,614 and Hiegel et al., *Sytitizetic Communications*, 15, 385–392 (1985) disclose that ketones may be chlorinated in the presence of TCIA. A Lewis acid catalyst is required. However, the use of substituted alkenes as substrate is not disclosed or suggested. Moreover, the issue of selectivity is not addressed; the reactions are usually performed in the presence of an excess of ketone, an undesirable procedure, especially when the carbonyl compound is a synthetic intermediate or when a separation of the substrate and the chlorinated product would be difficult. The process of the present invention permits selective chlorination of carbonyl compound precursors without requiring the presence of a large excess of substrate.

This invention provides a convenient process to α-cliloroketones, which are useful as fungicides or intermediates to fungicides, comprising the steps of chlorinating the substituted alkene in a solvent using trichloroisocyanuric acid to produce a chlorinated substituted alkene in a first step and subsequently hydrolyzing the chlorinated substituted alkene with an aqueous acid to produce the desired monochloroketone in a second step. The invention involves treatment of the substituted alkene with TCIA in a compatible solvent. The cyanuric acid by-product is removed by filtration or by washing with mild aqueous base. The chlorinated substituted alkene intermediate is then treated with aqueous acid in order to generate the monochloroketone product.

Specifically, this embodiment provides a process for the preparation of an α-chloroketone compound of formula (I) comprising the steps of (i) chlorinating a substituted alkene of formula (II) in a solvent using trichloroisocyanuric acid to produce a chlorinated substituted alkene of formula (III)

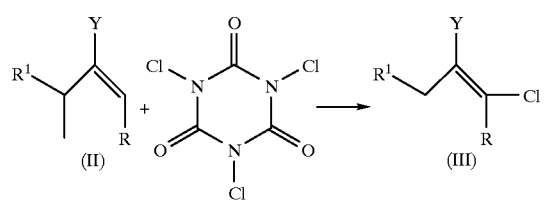

and (ii) hydrolyzing the chlorinated substituted alkene of formula (III) with an aqueous acid to produce the desired monochloroketone of formula (I)

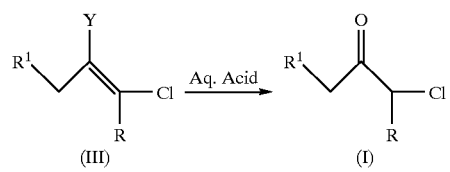

wherein

R and $R^1$ are each independently a hydrogen atom or alkyl, or R and $R^1$ together with the carbon atoms to which they are attached form a cyclic structure consisting of 5–7 atoms in the ring, Y is selected from the group consisting of $OR^2$, $NR^3R^4$, $OSiR^2R^5R^6$ and

and $R^2$, $R^3$, $R^4$, $R^5$ and $R^6$ are each independently alkyl groups, or $R^3$ and $R^4$ together with the nitrogen atom to which they are attached form a heterocyclic structure consisting of 5–6 atoms in the ring.

In this invention, alkyl means a $(C_1-C_8)$ straight or a $(C_3-C_8)$ branched chain alkyl group and includes, for example, methyl, ethyl, n-propyl, isopropyl, n-butyl, isobutyl, sec-butyl, tert-butyl, n-amyl, isoamyl, n-hexyl, isooctyl and the like.

Although a specific isomer is shown throughout for the compound of formula (III), it is to be understood that formula (III) actually represents a mixture of the cis and trans isomeric forms.

In a preferred form of this invention,

R and $R^1$ are each independently $(C_1-C_4)$alkyl, or R and $R^1$ together with the carbon atoms to which they are attached form a cyclic structure consisting of 5–6 atoms in the ring, Y is selected from the group consisting of $OR^2$, $NR^3R^4$, $OSiR^2R^5R^6$ and

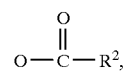

and $R^2$, $R^3$, $R^4$, $R^5$ and $R^6$ are each independently $(C_1-C_4)$ alkyl, or $R^3$ and $R^4$ together with the nitrogen atom to which they are attached form a heterocyclic structure selected from the group consisting of 1-piperidino, 1-(3-methylpiperidino), 1-(4-methylpiperidino), 1-pyrrolidino, 1-(3-methylpyrrolidino), 4-morpholino and 4-(2,6-dimethylmorpholino).

In a more preferred form of this invention,

R and $R^1$ are each independently $(C_1-C_4)$alkyl, or R and $R^1$ together with the carbon atoms to which they are attached form a cyclic structure consisting of 5–6 carbon atoms in the ring, Y is selected from the group consisting of $OR^2$, $NR^3R^4$, $OSiR^2R^5R^6$ and

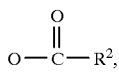

and $R^2$, $R^3$, $R^4$, $R^5$ and $R^6$ are each independently $(C_1-C_4)$ alkyl, or $R^3$ and $R^4$ together with the nitrogen atom to which they are attached form a heterocyclic structure selected from the group consisting of 1-piperidino, 1-pyrrolidino and 4-morpholino.

In an even more preferred form of this invention,

R and $R^1$ together with the carbon atoms to which they are attached form a cyclic structure consisting of 6 carbon atoms in the ring, Y is selected from the group consisting of $NR^3R^4$, $OSiR^2R^5R^6$ and

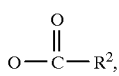

and $R^2$, $R^3$, $R^4$, $R^5$ and $R^6$ are each independently methyl or ethyl, or $R^3$ and $R^4$ together with the nitrogen atom to which they are attached form 1-pyrrolidino.

An additional feature of this invention is that TCIA functions as a convenient trapping agent for enol ether, enol ester or enamine compounds of formula (III) from compounds of formula (II).

A second additional feature of this invention is that when R is a hydrogen atom, the amount of TCIA which is employed in step (i) may be advantageously increased in order to form a dichlorinated substituted alkene of formula (IIIA) which is subsequently hydrolyzed in step (ii) to an (α,α-dichloroketoi-e of formula (IA) Therefore, this second additional feature provides a process for the preparation of an α,α-dichloroketone compound of formula (IA) comprising the steps of (i) chlorinating a substituted alkene of formula (II) in a solvent using trichloroisocyanuric acid to produce a chlorinated substituted alkene of formula (IIIA)

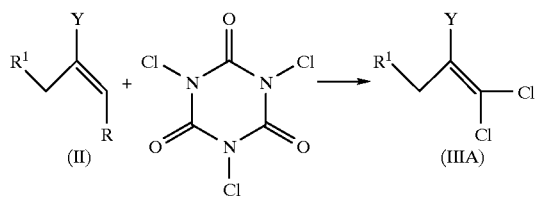

and (ii) hydrolyzing the chlorinated substituted alkene of formula (IIIA) with an aqueous acid to produce the desired dichloroketone of formula (IA)

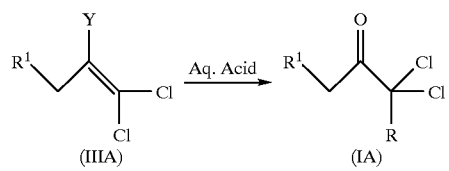

wherein

R is a hydrogen atom, $R^1$ is a hydrogen atom or alkyl,

Y is selected from the group consisting of $OR^2$, $NR^3R^4$, $OSiR^2R^5R^6$ and

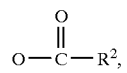

and $R^2$, $R^3$, $R^4$, $R^5$ and $R^6$ are each independently alkyl groups, or $R^3$ and $R^4$ together with the nitrogen atom to which they are attached form a heterocyclic structure consisting of 5–6 atoms in the ring.

The process of this invention is carried out by adding the TCIA, either as a solid or in solution, to a solution containing the substituted alkene. When monochlorination is desired, about 0.333 equivalent of TCIA is added per equivalent of alkene. When dichlorination is desired, $\geq 0.667$ equivalent of TCIA is added per equivalent of alkene. Reaction temperature may vary and can be above or below room temperature. Normally, a temperature of from about $-30°$ to about $100°$ C. is used. A preferred chlorination temperature is from about $0°$ to $70°$ C. More preferred in order to obtain the best chlorination selectivity is a temperature of about $50°$ C. or lower. Even more preferred is a temperature from $0°$ to $30°$ C. In some cases, particularly when using a silyl ether substrate, a lower temperature range, from about $-78°$ C. to about $0°$ C., is preferred to optimize selectivity for monochlorination. Compatible reaction solvents include hydrocarbons, halogenated hydrocarbons, aromatic compounds, esters, ethers, ketones and nitriles. When hydrocarbons are used as the solvent, elevated temperatures may be required. Preferred solvents include halogenated hydrocarbons, for example dichloromethane, esters, for example ethyl acetate, and ethers, for example ethyl ether. After chlorination is complete, the cyanuric acid by-product is removed by filtration, centrifugation, and/or by washing with a mild aqueous base such as sodium carbonate, sodium bicarbonate and the like. The intermediate may be hydrolyzed to the chloroketone product using a mild aqueous acid such as hydrochloric acid, sulfuric acid, trifluoroacetic acid, or an aqueous solution of methanesulfonic acid or toluenesulfonic acid. Aqueous hydrochloric acid or sulfuric acid are preferred. An acidic ion-exchange resin may also be utilized. When hydrochloric acid or sulfuric acid are used, additional water is usually added to facilitate the hydrolysis. The reaction temperature during this step is not critical. The chlorinated ketone product is recovered using standard methodology such as phase separation, washing, drying and isolation by concentration or crystallization.

The enol ether, enol ester, and enamine starting materials of formula (II) are readily available by treatment of a carbonyl compound precursor with an acid catalyst and the desired trapping agent. For example, treatment of a carbonyl compound with catalytic p-toluenesulfonic acid and acetic anhydride generates the corresponding enol ester, while treatment with an amine leads to enamine formation. These procedures are well known in the chemical literature. Enol ethers are generated by treatment of a carbonyl compound with a strong base, such as lithium diisopropylamide, sodium hydride and the like, followed by trapping with a trialkylsilyl halide, an alkyl halide or a dialkyl sulfate.

The following examples and experimental procedures are provided for guidance to the practitioner and are not meant to limit the scope of the invention which is defined by the claims.

EXAMPLE 1

Chlorination of Enol Acetate

To 5.0 g (35.6 mmol) of 1-acetyloxy-1-cyclohexene in 15 mL of dichloromethane was added portionwise at 0° C. 2.76 g (11.9 mmol) of trichloroisocyanuric acid (TCIA). After 2.5 h the reaction was incomplete based on gas chromatographic (GC) analysis and an additional 0.55 g (2.38 mmol) of TCIA was added and the reaction continued at room temperature overnight. Solids were removed by vacuum filtration and the filtrate evaporated to dryness in vacuo. The resultant oily residue was dissolved in 20 mL of ethyl acetate. Aqueous hydrochloric acid (5 mL of a 10% solution) was added and the reaction stirred at room temperature overnight. The phases were separated, the aqueous phase extracted with ethyl acetate (25 mL), the organics combined, dried over sodium sulfate, filtered and evaporated to dryness in vacuo. The resulting yellow oil (2.7 g, 20.4 mmol, 57%) was shown to be 2-chlorocyclohexanone by $^1$H NMR and GC/MS analysis.

EXAMPLE 2

Chlorination of Enamine

A solution of 5.0 g (33 mmol) of 1-pyrrolidino-1-cyclohexene contaminated with cyclohexanone was prepared using 20 mL of ethyl acetate. The solution was cooled to 0–5° C.; a solution of 2.55 g (11 mmol) of TCIA in 10 mL of ethyl acetate was added dropwise, keeping the temperature below 15° C. Once addition was complete the reaction was warmed to room temperature and stirred overnight. Solids were removed by vacuum filtration and the filtrate evaporated to dryness in vacuo. The resultant oily residue was disolved in 20 mL of ethyl acetate. Aqueous hydrochloric acid (10 mL of a 10% solution) was added and the reaction stirred at room temperature overnight. GC indicated the reaction was complete and contained a 3:2 mix of 2-chlorocyclohexane and cyclohexanone, the latter an impurity in the starting material.

EXAMPLE 3

Chlorination of Silyl Enol Ether

A solution of 1-(trimethylsilyloxy)cyclohexene (3.0 g, 17.6 mmol; 97% pure) in ethyl ether (20 mL) was chilled to –60° C. using a dry ice-acetone bath. Trichloroisocyanuric acid (1.38 g, 5.87 mmol) was dissolved in 8 mL of ethyl acetate, and the resulting solution was added over 2 h. After stirring for 30 minutes, the resulting slurry was filtered. The filtrate was treated with 1 M hydrochloric acid solution (2 mL). The reaction mixture was stirred until hydrolysis of the enol ether was complete. The solution was washed with saturated sodium bicarbonate solution and water, then dried over anhydrous sodium sulfate. The solvent was removed by evaporation under reduced pressure. The residue was dried under vacuum to yield 2-chlorocyclohexanone (2.01 g, 86%; 91% pure) as a pale yellow oil which crystallized upon standing in a refrigerator. The physical properties of the product were identical to that of an authentic standard purchased sample.

It is to be understood that changes and variations in this invention may be made without departing from the spirit and scope of this invention as defined by the appended claims.

We claim:

1. A process for the preparation of an α-chloroketone compound of formula (I) comprising the steps of (i) chlorinating a substituted alkene of formula (II) in a solvent using trichloroisocyanuric acid to produce a chlorinated substituted alkene of formula (III)

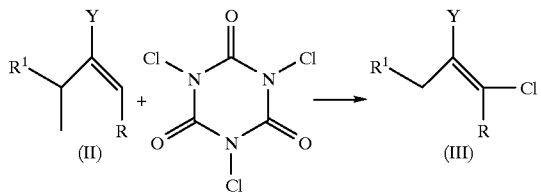

and (ii) hydrolyzing the chlorinated substituted alkene of formula (III) with an aqueous acid to produce the desired monochloroketone of formula (I)

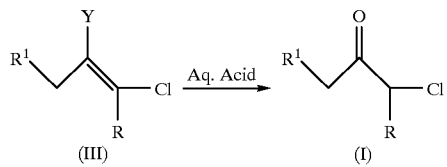

wherein

R and $R^1$ are each independently a hydrogen atom or alkyl, or R and $R^1$ together with the carbon atoms to which they are attached form a cyclic structure consisting of 5–7 atoms in the ring, Y is selected from the group consisting of $OR^2$, $NR^3R^4$, $OSiR^2R^5R^6$ and

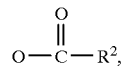

and $R^2$, $R^3$, $R^4$, $R^5$ and R6 are each independently alkyl groups, or $R^3$ and $R^4$ together with the nitrogen atom to which they are attached form a heterocyclic structure consisting of 5–6 atoms in the ring.

2. The process of claim 1 wherein

R and $R^1$ are each independently ($C_1$–$C_4$)alkyl, or R and $R^1$ together with the carbon atoms to which they are attached form a cyclic structure consisting of 5–6 atoms in the ring, Y is selected from the group consisting of $OR^2$, $NR^3R^4$, $OSiR^2R^5R^6$ and $$O-\overset{\overset{O}{\|}}{C}-R^2,$$

and

R², R³, R⁴, R⁵ and R⁶ are each independently (C₁–C₄) alkyl, or R₃ and R⁴ together with the nitrogen atom to which they are attached form a heterocyclic structure selected from the group consisting of 1-piperidino, 1-(3-methylpiperidino), 1-(4-methylpiperidino), 1-pyrrolidino, 1-(3-methylpyrrolidino), 4-morpholino and 4-(2,6-dimethylmorpholino).

3. The process of claim 2 wherein

R and R¹ are each independently (C₁–C₄)alkyl, or R and R¹ together with the carbon atoms to which they are attached form a cyclic structure consisting of 5–6 carbon atoms in the ring, Y is selected from the group consisting of OR², NR³R⁴, OSiR²R⁵R⁶ and $$O-\overset{\overset{O}{\|}}{C}-R^2,$$

and

R², R³, R⁴, R⁵ and R⁶ are each independently (C₁–C₄) alkyl, or R³ and R⁴ together with the nitrogen atom to which they are attached form a heterocyclic structure selected from the group consisting of 1-piperidino, 1-pyrrolidino and 4-morpholino.

4. The process of claim 3 wherein

R and R¹ together with the carbon atoms to which they are attached form a cyclic structure consisting of 6 carbon atoms in the ring, Y is selected from the group consisting of NR³R⁴, OSiR²P,⁵R⁶ and $$O-\overset{\overset{O}{\|}}{C}-R^2,$$

and

R², R³, R⁴, R⁵ and R⁶ are each independently methyl or ethyl, or R³ and R⁴ together with the nitrogen atom to which they are attached form 1-pyrrolidino.

5. A method of use of trichloroisocyanuric acid as a trapping agent for enol ether, enol ester or enamine compounds of formula (III)

(III)

from compounds of formula (II)

(II)

wherein

R and R¹ are each independently a hydrogen atom or alkyl, or R and R¹ together with the carbon atoms to which they are attached form a cyclic structure consisting of 5–7 atoms in the ring, Y is selected from the group consisting of OR², NR³R⁴, OSiR²R⁵R⁶ and $$O-\overset{\overset{O}{\|}}{C}-R^2,$$

and

R², R³, R⁴, R⁵ and R⁶ are each independently alkyl groups, or R³ and R4 together with the nitrogen atom to which they are attached form a heterocyclic structure consisting of 5–6 atoms in the ring.

6. A method of use of trichloroisocyanuric acid as a chlorinating agent for selective monochlorination of substituted alkenes selected from the group consisting of enol ethers, enol esters, enamines, 5-methylene-1,3-oxazin-2-ones, and 5-methylenlines.

7. A process for the preparation of an α,α-dichloroketone compound of formula (IA) comprising the steps of (i) chlorinating a substituted alkene of formula (II) in a solvent using trichloroisocyanuric acid to produce a chlorinated substituted alkene of formula (IIIA)

and (ii) hydrolyzing the chlorinated substituted alkene of formula (IIIA) with an aqueous acid to produce the desired dichloroketone of formula (IA)

wherein

R is a hydrogen atom,

R¹ is a hydrogen atom or alkyl,

Y is selected from the group consisting of OR², NR³R⁴, OSiR²R⁵R⁶ and

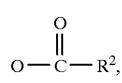
and
$R^2$, $R^3$, $R^4$, $R^5$ and $R^6$ are each independently alkyl groups, or $R^3$ and $R^4$ together with the nitrogen atom to which they are attached form a heterocyclic structure consisting of 5–6 atoms in the ring.
* * * * *